US00PP33954P2

(12) United States Plant Patent
Boxriker

(10) Patent No.: US PP33,954 P2
(45) Date of Patent: Feb. 15, 2022

(54) ***DAHLIA* PLANT NAMED 'KLEDH20215'**

(50) Latin Name: ***Dhalia* sp.**
Varietal Denomination: KLEDH20215

(71) Applicant: Klemm+Sohn GmbH & Co. KG, Stuttgart (DE)

(72) Inventor: Maike Boxriker, Schwäbisch Gmünd (DE)

(73) Assignee: KLEMM+SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 17/362,544

(22) Filed: Jun. 29, 2021

(51) Int. Cl.
*A01H 5/02* (2018.01)
*A01H 6/14* (2018.01)

(52) U.S. Cl.
USPC ..... Plt./321
CPC ..... *A01H 6/144* (2018.05)

(58) Field of Classification Search
USPC ..... Plt./321
CPC ..... A01H 6/144; A01H 5/02
See application file for complete search history.

*Primary Examiner* — Keith O. Robinson
(74) *Attorney, Agent, or Firm* — Weatherly IP Solutions, LLC; James M. Weatherly

(57) ABSTRACT

A new *Dahlia* plant designated 'KLEDH20215' particularly distinguished by a dark pink-purple flower color and a medium earliness, is disclosed.

1 Drawing Sheet

Genus and species: *Dahlia* sp.
Variety denomination: 'KLEDH20215'.

BACKGROUND OF THE NEW PLANT 'KLEDH20215'

The present invention comprises a new and distinct variety of *Dahlia*, botanically known as *Dahlia* sp., and hereinafter referred to by the variety name 'KLEDH20215'. 'KLEDH20215' originated from a controlled cross conducted in September 2016 in Stuttgart, Germany, between the proprietary female *Dahlia* 'DH-2015-2242' (not patented) and the proprietary male *Dahlia* 'DH-2015-2244' (not patented).

In May 2017, a seedling was selected and named 'KLEDH20215'. 'KLEDH20215' was first vegetatively propagated by vegetative cuttings in May 2017 in Stuttgart, Germany. 'KLEDH20215' was found to reproduce true to type in successive generations of asexual propagation.

SUMMARY OF 'KLEDH20215'

The following are the most outstanding and distinguishing characteristics of 'KLEDH20215' when grown under normal horticultural practices in Stuttgart, Germany.

1. Dark pink-purple flower color; and
2. Medium earliness.

DESCRIPTION OF THE PHOTOGRAPH

This new *Dahlia* plant is illustrated by the accompanying photograph of the plant approximately four months old and grown in a greenhouse in Stuttgart, Germany. The photograph shows the whole plant, unless otherwise noted, including the inflorescences and foliage and buds and was taken in July 2020 in Stuttgart, Germany. The colors shown are as true as can be reasonably obtained by conventional photographic procedures.

DESCRIPTION OF 'KLEDH20215'

The following detailed descriptions set forth the distinctive characteristics of 'KLEDH20215'. The data which define these characteristics were collected from asexual reproductions carried out in Latina, Italy. Data was collected on 15 week old plants potted at week five in May 2021 and grown in a plastic greenhouse. Color references are to The R.H.S. Colour Chart of The Royal Horticultural Society of London (R.H.S.), 5$^{th}$ edition (2007).

Classification:
- *Family*.—Asteraceae.
- *Botanical*.—*Dahlia* sp.
- *Designation*.—'KLEDH20215'.

Parentage:
- *Female parent*.—'DH-2015-2242' (unpatented).
- *Male parent*.—'DH-2015-2244' (unpatented).

Plant:
- *Plant and growth habit*.—Medium compact, upright. Well branched.
- *Plant height*.—22.0 cm.
- *Plant diameter or spread*.—37.0 cm.
- *Propagation type*.—Vegetative cuttings.
- *Time to produce a rooted young plant*.—3 to 4 weeks.
- *Rooting habit*.—Freely branching and moderately dense.
- *Root description*.—Fine and white.

Lateral branches:
- *Length*.—21.0 cm.
- *Diameter*.—0.4 cm.
- *Internode length*.—4.8 cm.
- *Aspect*.—Outwardly spreading.
- *Strength*.—Strong.
- *Texture*.—Smooth.
- *Color*.—RHS 148A.

Foliage:
- *Arrangement*.—Leaves are opposite on the branches.
- *Length*.—7.2 cm.
- *Width*.—5.2 cm.
- *Shape*.—Rhomboid.
- *Apex*.—Acute.
- *Base*.—Acute.
- *Margin*.—Sinuate.

*Venation pattern*.—Dichotomous.
*Venation color*.—RHS 148A.
*Texture*.—Upper surface: Smooth. Lower surface: Weakly rugose.
*Color*.—Immature: Upper surface: RHS N137A. Lower surface: RHS 138B. Mature: Upper surface: RHS N137B. Lower surface: RHS 138B.

Petioles:
*Length*.—2.0 cm.
*Diameter*.—0.3 cm.
*Texture* (*both surfaces*).—Smooth.
*Color*.—Upper surface: RHS 152A. Lower surface: RHS 146C.

Inflorescence:
*Appearance and arrangement*.—Daisy-eyed double inflorescences held above the foliage.
*Fragrance*.—Medium.
*Time to flower*.—About 70 days after potted a rooted cutting.
*Post-production longevity*.—Plants flower continuously from spring through autumn.

Inflorescence bud:
*Height*.—0.5 cm.
*Diameter*.—1.2 cm.
*Shape*.—Circular.
*Color*.—RHS 176A.

Inflorescence size:
*Diameter*.—7.0 cm.
*Depth* (*height*).—3.5 cm.
*Disc diameter*.—1.0 cm.
*Receptacle height*.—0.6 cm.
*Receptacle diameter*.—1.1 cm.
*Receptacle color*.—RHS 138A.

Ray florets:
*Quantity per inflorescence*.—About 50.
*Length*.—3.6 cm.
*Width*.—2.0 cm.
*Shape*.—Oval.
*Apex*.—Obtuse.
*Base*.—Acute.
*Margin*.—Entire.
*Aspect*.—Semi-Upright.
*Texture*.—Upper surface: Smooth. Lower surface: Weakly rugose.
*Color*.—Immature: Upper surface: RHS 61B. Lower surface: RHS 64B. Mature: Upper surface: RHS 61B. Lower surface: RHS 64B.

Disc florets:
*Quantity per inflorescence*.—About 34.
*Length*.—1.6 cm.
*Diameter*.—0.2 cm.
*Shape*.—Tubular.
*Texture* (*both inner and outer surfaces*).—Smooth.
*Color*.—Immature: Inner surface: RHS 173A. Outer surface: RHS 183A. Mature: Inner surface: RHS 173A. Outer surface: RHS 185A.

Phyllaries:
*Quantity per inflorescence*.—40.
*Length*.—2.0 cm.
*Width*.—0.7 cm.
*Shape*.—Elliptic.
*Apex*.—Truncate.
*Base*.—Truncate.
*Margin*.—Entire.
*Texture*.—Upper surface: Smooth. Lower surface: Smooth.
*Color*.—Upper surface: RHS 59C. Lower surface: RHS 59C.

Peduncles:
*Length, terminal peduncle*.—13.0 cm.
*Length, axillary peduncle*.—7.5 cm.
*Diameter*.—0.3 cm.
*Aspect*.—Semi-upright.
*Strength*.—Strong.
*Texture*.—Smooth.
*Color*.—RHS 165A.

Reproductive organs:
*Androecium*.—Present on disc florets. Quantity per floret: 4. Filament length: 0.9 cm. Filament color: RHS 1B. Anther shape: Lanceolate. Anther length: 0.4 cm. Anther color: RHS 14A. Pollen amount: Medium. Pollen color: RHS 17A.
*Gynoecium*.—Present on disc florets. Quantity per floret: 1. Pistil length: 1.2 cm. Style length: 0.6 cm. Style color: RHS 1A. Stigma shape: Lanceolate. Stigma color: RHS 17A. Ovary color: RHS 1B.

Fruit and seed set: No fruit or seed set observed.

Disease and pest/insect resistance: No disease resistance observed.

COMPARISON OF 'KLEDH20215' WITH PARENTAL LINES AND KNOWN VARIETY

'KLEDH20215' is distinguished from the parents as described in Table 1.

TABLE 1

Comparison with Parental Line

| Characteristic | 'KLEDH20215' | Female Parent 'DH-2015-2242' | Male Parent 'DH-2015-2244' |
|---|---|---|---|
| Flower color | Dark pink purple | Pink | Pink Lavender |

'KLEDH20215' can be compared to the commercial *Dahlia* variety 'KLEDH18010' (U.S. Plant Pat. No. 32,428). Differences between the varieties are described in Table 2.

TABLE 2

Comparison with Similar Variety

| Characteristic | 'KLEDH20215' | 'KLEDH18010' |
|---|---|---|
| Earliness | Medium early | Late |
| Flower color | Dark pink-purple | Red |

I claim:

1. A new and distinct variety of *Dahlia* plant designated 'KLEDH20215', as illustrated and described herein.

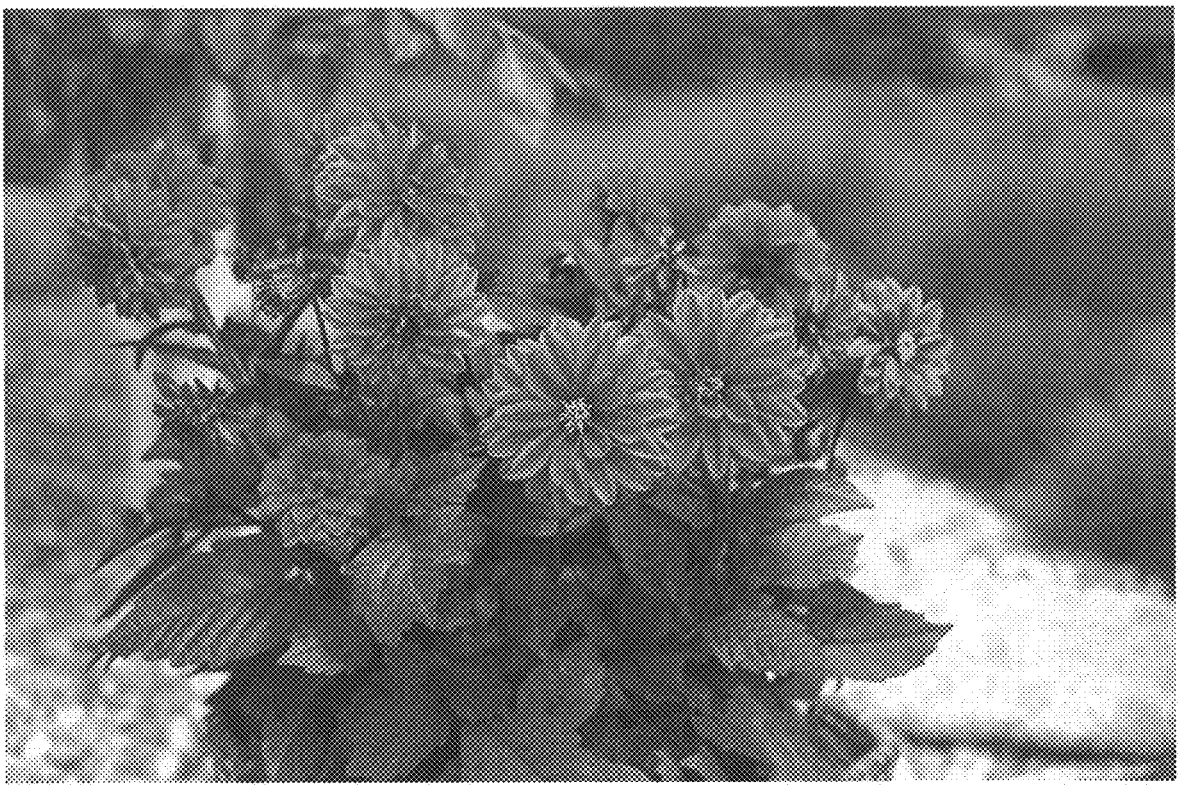

* * * * *